United States Patent [19]

Franetzki et al.

[11] 4,282,872
[45] Aug. 11, 1981

[54] DEVICE FOR THE PRE-PROGRAMMABLE INFUSION OF LIQUIDS

[75] Inventors: Manfred Franetzki, Uttenreuth; Klaus Gagneur, Bubenreuth; Karl Prestele, Erlangen, all of Fed. Rep. of Germany

[73] Assignee: Siemens Aktiengesellschaft, Berlin & Munich, Fed. Rep. of Germany

[21] Appl. No.: 969,189

[22] Filed: Dec. 13, 1978

[30] Foreign Application Priority Data

Dec. 28, 1977 [DE] Fed. Rep. of Germany ....... 2758467

[51] Int. Cl.³ ............................................ A61M 37/00
[52] U.S. Cl. ................................................ 128/213 R
[58] Field of Search ........... 128/213 R, 214 E, 214 F, 128/260

[56] References Cited

U.S. PATENT DOCUMENTS

| 3,809,871 | 5/1974 | Howard et al. | 128/214 E |
|---|---|---|---|
| 4,048,474 | 9/1977 | Olesen | 128/214 E |
| 4,077,405 | 3/1978 | Haerten et al. | 128/214 F |

FOREIGN PATENT DOCUMENTS 2451424 5/1976 Fed. Rep. of Germany .

*Primary Examiner*—William E. Kamm
*Attorney, Agent, or Firm*—Hill, Van Santen, Steadman, Chiara & Simpson

[57] ABSTRACT

Particularly for diabetes therapy, it is desirable to continuously infuse insulin in different rates into the body of the patient, because the insulin requirements of the diabetic are subject to great fluctuations. Therefore, a control device serves as the program transmitter for a microdosing unit. The control device for the microdosing unit has memory means for a prescribable control program allocated to it, whereby the control program can be called up directly by the patient at the control device. The program sequence of the infusion is started only by means of the dialing-up of a plurality of insulin units to be delivered into the body or of relevant food values taken in by the patient with a meal and of a starting time ($T_1$, $T_2$). In addition, specific base rates of the infusion can be selected by the patient. With the invention device, diabetes patients can call up the necessary insulin administration according to short programs at meals.

9 Claims, 7 Drawing Figures

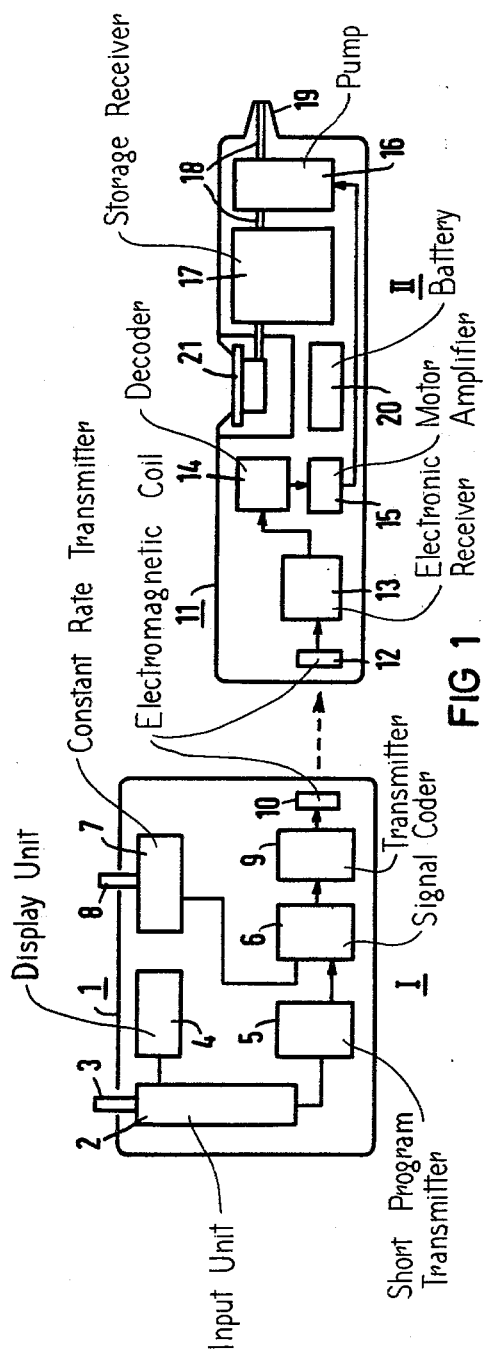
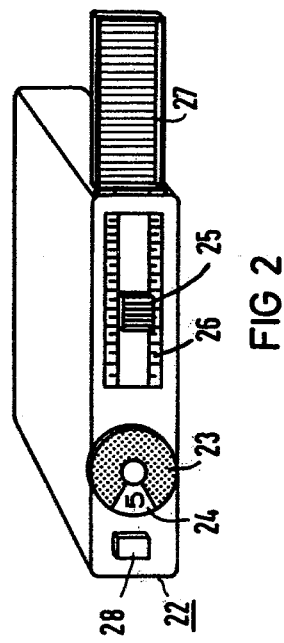

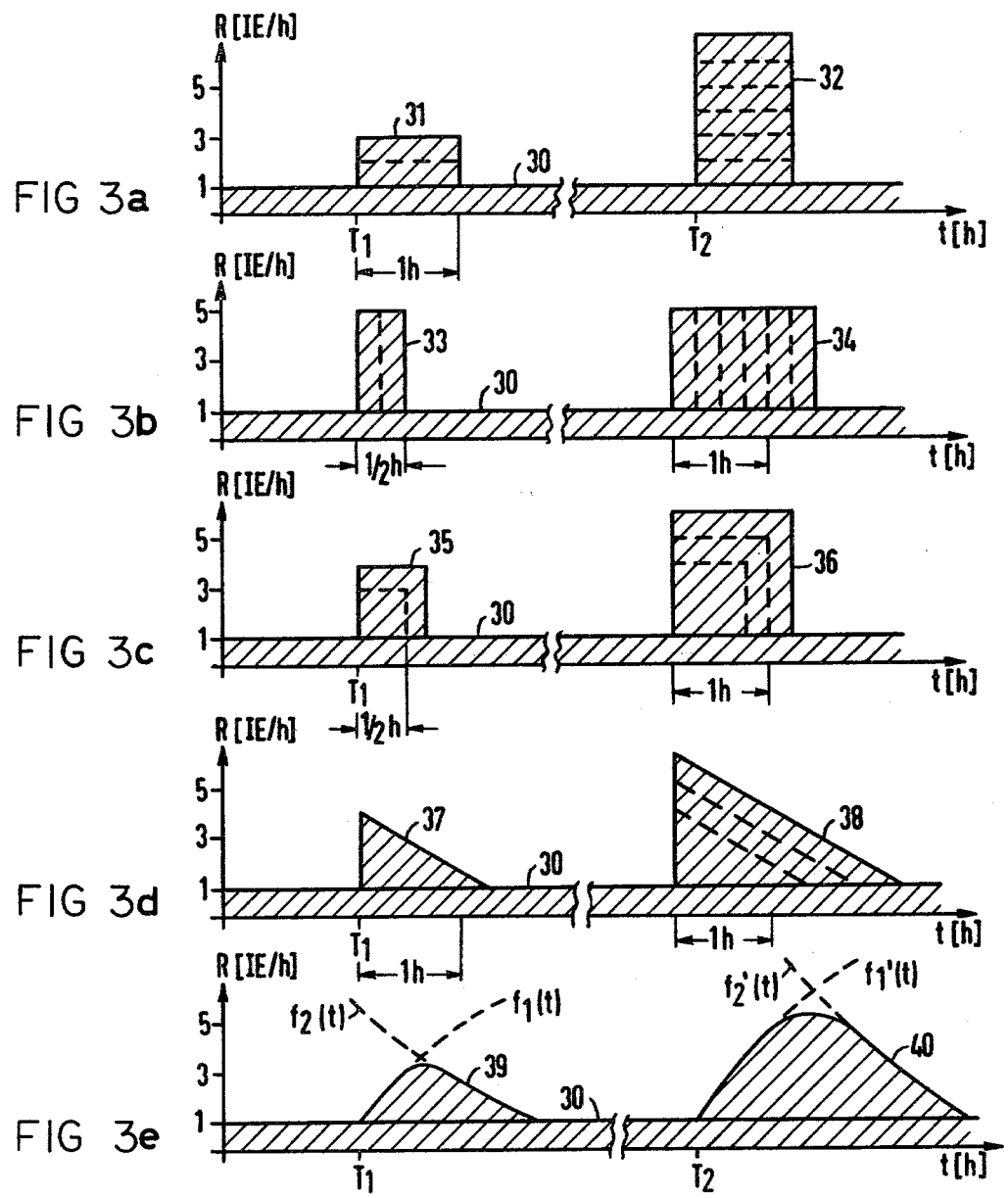

DEVICE FOR THE PRE-PROGRAMMABLE INFUSION OF LIQUIDS

CROSS-REFERENCE TO RELATED APPLICATION

The present application relates to an improvement with respect to our copending application for patent U.S. Ser. No. 969,200 filed Dec. 13, 1978, and entitled "Device For The Pre-Programmable Infusion Of Liquids," and this application is incorporated herein by reference.

BACKGROUND OF THE INVENTION

The invention relates to a device for the pre-programmable infusion of liquids into the human or animal body, particularly for the administration of insulin in diabetes therapy, consisting of a microdosing unit for the liquid as well as a control device as a program transmitter for the microdosing unit. Thereby, the microdosing unit for the liquid can be implanted in the body together with or separate from the control device or can also be carried externally on the body surface.

In diabetes therapy, it is desirable to continuously infuse insulin into the body of the patient in varying installments, because the need of the diabetic for insulin during the day is subject to great fluctuations, determined, for example, by the rhythm of the meals. It has been shown that—as long as no infusion devices that regulate themselves automatically by means of glucose sensors are available—the delivery of insulin should best ensue according to a daily profile that can be individually adjusted and pre-programmed for the patient. Thereby, it is possible, in a device of the type initially cited, to allocate memory means for a prescribable control program at least to the control device for the microdosing unit, whereby the control program is pre-programmable in discrete time steps corresponding to the 24-hour daily sequence at an external programming device and the control device is electrically connected to the programming device or a program carrier, respectively, solely for the transfer of the pre-programmed control program. Such a device has the advantage that the pre-programming of the daily profile can be carried out in a simple and clear manner by the physician; for example, such devices can then be used when, during a longer examining period when the patient is in the hospital under the supervision of the physician, an optimum daily infusion profile for a subsequent infusion installation to be completely implanted or also for a later, standard injection therapy is to be ascertained. However, in this case the patient in general has no direct access for altering the pre-programmed dosage and is, therefore, bound to a relatively regular daily course with the ingestion of his meals predetermined both in terms of time and amount.

In certain cases of diabetes, however, binding the patient to a regular daily course is not absolutely necessary. Based on the constitution of the patient, it can be possible that the patient can pursue a relatively irregular daily course insofar as the necessary insulin doses are administered to him at the necessary times at meals. In such a case, therefore, the constraint of the patient to the daily profile of the pre-programmed insulin administration is unnecessary and can even become a burden for the patient.

SUMMARY OF THE INVENTION

The object of the invention is therefore to create a further device of the type initially cited with which, on the one hand, a pre-programmed infusion is made possible, but which, on the other hand, leaves the patient a certain freedom in the time of ingesting meals. The programmed sequence of the infusion should indeed correspond with the actual infusion requirement as far as possible, but be able to be temporally influenced by the patient.

The object is inventively achieved in that the control device for the microdosing unit has memory means for a prescribable control program allocated to it, which control program can be directly called up by the patient at the control device, and in that the programmed sequence of the infusion is started only through the dialing-up of a plurality of the insulin units to be emitted into the body or of the carbohydrate units ("bread units") taken in by the patient with the meal, respectively, and a starting time.

With the invention, therefore, a possibility is created to combine the advantages of devices for pre-programmable infusion with the possibility of a delivery of infusion liquid that is variable in terms of time and amount. At a meal or at the end of a meal, the patient only selects an equivalent amount of insulin units corresponding to the "bread units" taken in at the meal on the control device which he carries, whereby in so doing a pre-programmed control program covering a number of hours is called up from a program transmitter.

In an advantageous embodiment of the invention, on the one hand a constant base rate is adjusted at the control device, to which the additional insulin administrations are superimposed as a rectangular pulse-rate versus time function as needed at a meal. In this case, either the delivery time or the pulse rate is predetermined as constant, so that the programmed sequence ensues only by means of the selection of the other parameter which determines the area encompassed by the rectangular function i.e. the insulin amount dispensed over the total delivery time. As an alternative, by means of prescribing rectangle functions with changeable amplitude and width upon the dialing-up of an n-fold insulin amount, in any given case the ratio of infusion time and rate can also be changed.

In a further advantageous embodiment of the invention, the control program of the infusion rate essentially corresponds to a triangular pulse rate versus time function, for example, right-angled triangle, whereby the infusion rate quickly rises from a base value to the highest value and subsequently decreases again from the highest value to the base value with a predetermined functional dependency. Thereby, the rate of decrease is preferably linear as a function of the predetermined initial increase. But the decrease as a function of time can also be exponential in the manner of an e-function. The infusion rate output can, of course, also be constructed more complexly in terms of its variation with time and resultant total area and be matched to the actual insulin delivery of a natural pancreas, whereby upon erection of a profile with nonlinear functional dependencies a computer (microprocessor) is to be provided for matching the dialed-up infusion amount to the delivery profile.

The infusion device created with the invention preferably consists of two individual devices. Thereby, the microdosing unit can be optionally designed as an implant with transcutaneous signal transmission from the control device to be carried on the exterior of the body or as a device to be arranged on the exterior of the body along with the control device. In the latter case, a direct line connection for signal transmission between the two devices is then possible. Further advantages and details of the invention derive from the following descriptions of sample embodiments on the basis of the accompanying sheets of drawings in conjunction with the further subclaims; and other objects, features and advantages will be apparent from this detailed disclosure and from the appended claims.

BRIEF DESCRIPTION OF THE DRAWINGS

FIG. 1 is a basic representation of a control device and a microdosing unit with block diagrams therein to show the individual functional units;

FIG. 2 is an exterior view of a control device in perspective representation; and FIG. 3 comprising FIGS. 3a–3e shows various pulse diagrams for possible program-wise predetermined infusion rates of the insulin delivery.

DETAILED DESCRIPTION

In FIG. 1, a control device is indicated at I and a microdosing unit at II. The control device I consists of a device housing 1 about the size of a pocket calculator, which accepts the electronic component parts and whose operation is selectable from the outside by means of a plurality of operating elements. In an input unit 2, the number of insulin units to be delivered is selected via an actuating member 3, said number of insulin units being visible on the device housing 1 at a display unit 4. A short program transmitter 5 is controlled by the input unit 2, in which short program transmitter program sequences between about 0.5 and 3 hours for the infusion rate are stored, which are started by means of being fetched with the input of the insulin units to be delivered. As the program transmitter 5, for example, digital semiconductor memories, so-called RAM's, are used which are programmable for program sequences as desired. The program transmitter 5 controls a signal coder 6 which appropriately prepares the selected program for signal transmission. The signal coder 6 is further controllable by a constant rate transmitter 7 with actuation member 8. The coded signals are delivered from the signal coder 6 to a transmitter 9 with which an electromagnetic coil 10 is controlled by means of remote control.

In the sample embodiment, the control signals are to be transmitted wirelessly, and, indeed, inductively. Instead of an inductive signal transmission, of course, other electromagnetic signal transmission processes for example infrared or ultrasonic signal transmission processes are also possible. As an alternative to that, in an extracorporeal arrangement of the microdosing unit, the control device can also be coupled to the microdosing unit via a direct electric line connection.

The housing of the microdosing unit II is indicated at 11. Analogous to the control device I, it contains a receiver coil 12 with an electronic receiver 13 and decoder 14 connected on the output side. A motor amplifier 15 is controlled via the decoder 14, with which motor amplifier the drive motor of a mechanical pump 16 is driven. By means of the pump 16, the liquid insulin is conveyed out of a storage reservoir 17 to a catheter connection 19 on the device housing 11 via a connection line 18. Further, the housing 11 of the microdosing unit I also contains a battery 20 as an energy source for the pump drive as well as a refilling valve 21, via which insulin can be refilled into the storage reservoir 17 by means of an injection through a membrane that automatically closes itself—transcutaneously in the case of an implanted microdosing unit, if necessary.

In FIG. 2, the housing of a control device is indicated at 22. A rotary switch 23 is located on its side face, with which discrete infusion amounts are selected in insulin units (for example, in steps from 1 through 10 IE) represented by indicia on a selector dial 24, which infusion amounts are input into the program transmitter 5. A sliding switch 25 is arranged next to it, with which constant base rates of the insulin delivery (for example adjustable between 0.4 and 2 IE/h) can be adjusted on a scale 26. Since, in general, the base rate is only prescribed once and is then not to be changed again for a longer time, the scale 26 is covered by a flap 27 in the operating state of the control device.

In the pulse diagrams according to FIG. 3, the flow rate of the microdosing unit II is illustrated for various short programs as a function of time. In each case, the straight line 30 parallel to the abscissa indicate that a constant base rate for the delivery of insulin units is adjusted, namely 1 IE/h. In the pulse diagram of FIG. 3a, the delivery rate at the selecting time $T_1$ rises from 1 IE/h to 3 IE/h and after an hour again decreases to the initial value. At the selection time $T_2$, the delivery rate rises to an infusion rate of 7 IE/h and after an hour again decreases to the initial value. The rectangles 31 or 32, respectively, superimposed on the constant delivery rate correspond to a total insulin delivery of 2 IE or 6 IE, respectively. For such a delivery, thus, only the delivery time of one hour is stored in the program transmitter 5. After his meal (at time $T_1$ or $T_2$), the patient then need only select the required insulin units on switch 23, whereupon the delivery rate changes for the prescribed time span.

In the pulse diagram of FIG. 3b, on the other hand, the delivery rate is given as a constant. By means of selecting the insulin units on switch 23, the time span of the insulin delivery, which is changeable from, for example, 0.5 through 3 hours, is then determined by the program transmitter. In this case, the rectangles 33 or 34, respectively, again indicate superimposed values of 2 IE or 6 IE, respectively.

In the pulse diagram of FIG. 3c, a primary rectangle with the edge length and height, $t = 0.5$ h and $I = 2$ IE/h is constructed. Such a rectangle is storable in program transmitter 5 as a square function with corresponding scaling. Upon doubling of the area of such a scaled primary square function, the edge lengths and heights in any given case change in the ratio $\sqrt{2}:1$. Accordingly, the squares 35 or 36, respectively, again indicate 2 IE or 6 IE, respectively. A multiplication of the insulin amount by the factor n, accordingly, produces a change of the delivery time and delivery rate by the factor $\sqrt{n}$.

In the pulse diagram of FIG. 3d, at time $T_1$ the delivery rate is increased from the base value 1 IE/h to a value of 4 IE/h and thereafter decreases linearly with a prescribed slope to the initial value. At time $T_2$, the delivery rate is increased to a value of 6 IE/h, from where it likewise again returns to the initial value with the same prescribed slope. In this case, thus, congruent triangles are set up to represent the functions in each case on the constant base rate, whereby the triangle 37 again corresponds to 2 IE and the triangle 38 to 6 IE. Accordingly, the delivery rates and times change in a tripled delivery by increasing each of the triangle sides representing delivery rate and time in the ratio $\sqrt{3}$, whereby the slope of the hypotenuse of the triangle is stored in the program transmitter. Instead of the straight lines, an e-function can also be provided for the decrease of the infusion rate from the highest value to the base value. The insulin delivery in a triangular form has the advantage, particularly, that the transition from the increased delivery rate to the normal base rate does not occur abruptly, but rather gradually in a time-continuous manner.

If one analyzes the actual insulin requirements in the case of a meal and subsequent digestion in detail, then, corresponding to the insulin delivery of a natural pancreas, one first obtains a quick increase to a highest value with a superimposed peak and a subsequent slow decrease to the initial value in the manner of e-functions. This actual need, however, can only be matched by means of several exponential functions, whereby the encompassed area is then naturally more complex to realize. Such a course of the delivery rate is illustrated in a simplified manner in the pulse diagram of FIG. 3e with two adapted functions. The delivery rates are determined by means of the exponential functions $f_i{}^k(t)$, whereby the free parameters are adaptable as desired. In such a case, however, the program transmitter must have a computer, for example, a microprocessor, allocated to it, which adapts the infusion amount selected by the patient, i.e. a given total surface area, to the surface area actually desired with prescribed contours corresponding to the functional dependency stored in the program transmitter.

It has turned out that in specific individual cases—for example after a meal that is difficult to digest—it can be necessary to vary the delivery time in deviation from the pre-programmed short program. In the pulse diagram according to FIG. 3d, this means, for example, that the slope of the straight lines is changeable. To this end, then, a further step-switch 28 for time retardation is provided on the control device according to FIG. 2, with which the patient can adjust a time scale of the program to correspond with the digestibility and resorption of an ingested meal.

In the device according to German Offenlegungsschrift No. 2,451,424, the daily sequence of the infusion is pre-programmable on the programming panel of a control unit. By means of such a pre-programming, the infusion device delivers a constant base rate and, upon need, a peak rate superimposed upon this base rate, for example, according to FIGS. 2 or 3 of the U.S. Pat. No. 4,077,405. In such a control, the patient is forced to arrange his day with the ingestion of meals, etc., according to the pre-programmed daily program.

The invention eliminates these disadvantages in that the patient can call up short programs at any desired times corresponding to the requirements existing at any given time. Thereby, specifically for diabetes therapy, the patient need only select the amount of the required insulin units (IE) or the bread units (BE) taken in with a meal, respectively, in order to let the infusion proceed according to the desired program. (The abbreviation "IE" stands for "Internationale Einheit" in German, or international unit in English. The abbreviation BE is a recognized abbreviation in German medical practice, referring to a unit for calculating the amount of carbohydrate for the diet, e.g. in the case of diabetes.)

It will be apparent that many modifications and variations may be effected without departing from the scope of the novel concepts and teachings of the present invention.

We claim as our invention:

1. Apparatus for the pre-programmable infusion of liquids into a patient's body, comprising
    a microdosing unit having supply means for supplying the liquid at a controllable infusion rate in response to programming signals,
    a control device operable for supplying selected programming signals to said microdosing unit for correspondingly controlling the rate of supply of the liquid thereby,
    said control device having program storage means (5) for storing at least one predeterminable control program (31-40), which provides for the generation of respective different programmed sequences of infusion amounts as a function of time, each of the respective different programmed sequences of infusion amounts as a function of time providing for the delivery of a respective different total liquid amount by said supply means over a relatively short time span of not more than three hours, with the different total liquid amounts lying within a predetermined available range of amounts suitable for selection by the patient,
    said program storage means (5) being controllable by each of a respective series of manually generated selection signals each representing a respective different one of said total liquid amounts to be infused within said available range of amounts and beginning at a given starting point, to generate the respective corresponding one of said programmed sequences of infusion amounts as a function of time over the relatively short time span thereof in accordance with said one control program stored therein, such that the respective corresponding total liquid amount is supplied by said microdosing unit in said relatively short time span,
    said control device having manually actuatable control means (3, 23) coupled with said program storage means (5) and being selectively manually actuable by the patient to respective positions corresponding to respective total liquid amounts within said available range of amounts to supply respective ones of said series of said manually generated selection signals and to supply the given starting time to the program storage means (5), whereby the microdosing unit is responsive to patient manual selection of one of said total liquid amounts from said available range of amounts and a desired starting point based on actual real time patient need while supplying such patient-selected total amount over a relatively short time span and at a rate as a function of time which can be pre-programmed by the patient's physician according to the characteristics of the individual patient.

2. Apparatus according to claim 1, with the liquid supplied by said supply means being insulin, and said manually actuatable control means having indicia means for providing a display in accordance with the amount of insulin to be supplied in each of the respective positions of said manually actuatable control means.

3. Apparatus according to claim 1, with the liquid supplied by said supply means being insulin, and said control device having constant rate transmitting means (7) for controlling said microdosing unit to supply insulin at a constant base rate (30), the respective different programmed sequences of infusion amounts as a function of time provided for by said program storage means (5) being superimposed on said constant base rate (30).

4. Apparatus according to claim 3, with said constant rate transmitter means (7) having manually adjustable means accessible for manual actuation to effect adjustment of said constant base rate (30) within a predetermined range.

5. Apparatus according to claim 1, with the liquid supplied by said supply means being insulin, and said control program stored by said program storage means (5) representing a delivery profile specifically corresponding to the insulin requirements of the patient during digestion.

6. Apparatus according to claim 1, with said control program stored by said program storage means (5) providing for the generation of essentially rectangular waveform programmed sequences (31, 32) as a function of time, said manually actuatable control means in its respective positions selecting respective different amplitudes for said essentially rectangular waveform programmed sequences (31, 32).

7. Apparatus according to claim 1, with said control program stored by said program storage means (5) providing for the generation of essentially rectangular waveform programmed sequences (33, 34) as a function of time, said manually actuatable control means in its respective positions selecting respective different time durations for said essentially rectangular waveform programmed sequences (33, 34).

8. Apparatus according to claim 1, with said control program stored by said program storage means providing for the generation of essentially rectangular waveform programmed sequences (35, 36) as a function of time, said manually actuatable control means in its respective positions selecting respective different values of both amplitude and time duration for said essentially rectangular waveform programmed sequences (35, 36).

9. Apparatus according to claim 1, with said control program stored by said program storage means providing for the generation of essentially triangular waveform programmed sequences (37–40) as a function of time, said manually actuatable control means in its respective positions selecting respective different values of both peak amplitude and time duration for said essentially triangular waveform programmed sequences (37–40).

* * * * *